United States Patent [19]

Fischer et al.

[11] 3,946,048

[45] Mar. 23, 1976

[54] 2-OXY AND 2-THIO-2,3-DIHYDROBENZOFURANYL-5-AMINOSULFONATES

[75] Inventors: Adolf Fischer, Mutterstadt; Wolfgang Rohr, Mannheim, both of Germany

[73] Assignee: BASF Aktiengesellschaft, Ludwigshafen (Rhine), Germany

[22] Filed: May 13, 1974

[21] Appl. No.: 469,063

[30] Foreign Application Priority Data

May 16, 1973 Germany............................ 2324592

[52] U.S. Cl. 260/346.2 R; 260/268 FT; 260/293.58; 260/326.82; 260/346.2 M; 260/247.1 S; 71/88; 71/92; 71/94; 71/95
[51] Int. Cl.² ........................................ C07D 307/83
[58] Field of Search .............. 260/346.2 R, 346.2 M

[56] References Cited
OTHER PUBLICATIONS

Binkley et al., J. Am. Chem. Soc., Vol. 61, 1939, pp. 3250–3251.
Cram et al., Organic Chemistry, New York, McGraw–Hill, 1959, p. 217.

Primary Examiner—John D. Randolph
Assistant Examiner—Bernard I. Dentz
Attorney, Agent, or Firm—Johnston, Keil, Thompson & Shurtleff

[57] ABSTRACT

New and valuable 5-benzofuranyl esters having a good herbicidal action; herbicides containing these compounds as active ingredients; and a process for controlling the growth of unwanted plants with these compounds.

52 Claims, No Drawings

2-OXY AND 2-THIO-2,3-DIHYDROBENZOFURANYL-5-AMINO-SULFONATES

The present invention relates to new and valuable 5-benzofuranyl esters, their use as herbicides, and herbicides containing these compounds as active ingredients.

It is known (German Laid-Open Application DOS 1,926,139) to use 2,3-dihydro-3,3-dimethyl-2-ethoxy-5-benzofuranylmethanesulfonate as a herbicide. However, its action is poor.

We have now found that 5-benzofuranyl esters of the formula

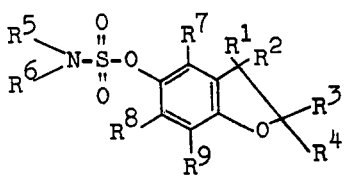

where $R^1$, $R^2$ and $R^3$ are identical or different and each denotes hydrogen or alkyl (methyl, ethyl, propyl) or $R^1$ and $R^2$ together, or $R^2$ and $R^3$ together, form an alkylene chain (e.g., with from 2 to 5 carbon atoms); $R^4$ denotes hydroxy, alkoxy (e.g., with from 1 to 5 carbon atoms, and optionally substituted by halogen or alkoxy, e.g., methoxy, ethoxy, β-chloroethoxy and methoxyethoxy), alkenyloxy (e.g., of from 2 to 4 carbon atoms and optionally substituted by halogen, e.g., allyloxy and chloroallyloxy), alkynyloxy (e.g., of from 2 to 4 carbon atoms and optionally substituted by halogen, e.g., propargyloxy, butynyloxy and chlorobutynyloxy), alkylmercapto (e.g., methylmercapto, ethylmercapto and propylmercapto), aralkylmercapto (optionally substituted in the aromatic portion by halogen or alkyl, e.g., benzymercapto benzylmercapto, -phenylethylmercapto, p-chlorobenzylmercapto), aryloxy (optionally substituted by halogen or nitro, e.g., phenoxy and nitrophenoxy), $R^4$ further denotes the group $NR^{10}R^{11}$, where each of $R^{10}$ and $R^{11}$ is alkyl (methyl, ethyl, propyl, butyl) or substituted alkyl (e.g., of from 1 to 4 carbon atoms and substituted by halogen or alkoxy, e.g., haloethyl and methoxyethyl) or $R^{10}$ and $R^{11}$, together with the nitrogen atom whose substituents they are, form a heterocyclic ring, which optionally bears substituents, e.g., morpholine, 2,6-dimethylmorpholine, pyrrolidine, piperidine, methylpiperazine, hexamethyleneimine, 2-methylhexamethylenimine, azetidine and trimethylazetidine, $R^4$ further denotes the group $OCOR^{12}$, where $R^{12}$ denotes alkyl (e.g., of from 1 to 4 carbon atoms and optionally substituted by halogen, e.g., methyl, ethyl, propyl, trifluoromethyl and chloromethyl), alkenyl (e.g. allyl and methallyl), alkynyl (e.g., propargyl and butynyl), aryl (optionally substituted by halogen, alkyl or nitro, e.g., phenyl, tolyl, chlorophenyl and nitrophenyl), alkylamino (e.g., methylamino and dimethylamino), alkoxy (optionally substituted by halogen or alkoxy, e.g., methoxy, ethoxy and propoxy), alkenyloxy (of 3 or 4 carbon atoms, optionally substituted by halogen, e.g., allyloxy and chloroallyloxy), alkynyloxy (e.g., of 3 or 4 carbon atoms and optionally substituted by halogen, e.g., propargyloxy and chlorobutynyloxy), arylamino (optionally substituted by alkyl, chloro or alkoxy, e.g., phenylamino, tolylamino and chlorophenylamino), or aryloxy (optionally substituted by alkyl or halogen, e.g., phenoxy, tolyloxy and chlorophenyloxy), $R^5$ and $R^6$ are identical or different and each denotes hydrogen, alkyl (methyl, ethyl, propyl, isopropyl, butyl, sec-butyl, isobutyl) or substituted alkyl (β-chloroethyl), and $R^7$, $R^8$ and $R^9$ are identical or different and each denotes hydrogen, alkyl (methyl, ethyl), halogen (chloro, bromo), cyano, acetyl or methoxy, have a herbicidal action superior to that of conventional herbicides.

The new compounds are prepared by reacting a benzofuranyl derivative of the formula

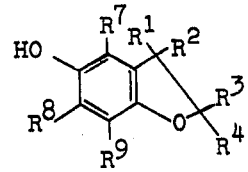

where $R^1$, $R^2$, $R^3$, $R^4$, $R^7$, $R^8$ and $R^9$ have the above meanings, with an aminosulfonyl halide of the formula

where $R^5$ and $R^6$ have the above meanings and X denotes halogen, in the presence or absence of an acid acceptor.

The preparation of the new 5-benzofuranyl esters is illustrated by the following examples.

EXAMPLE 1

At 0° to 5°C and with stirring, 36 parts (by weight) of methylaminosulfonyl chloride is added to a solution of 48.8 parts of 2,3-dihydro-3,3-dimethyl-2-morpholino-5-hydroxybenzofuran and 27.3 parts of triethylamine in 130 parts of tetrahydrofuran. The mixture is stirred for 1 hour at room temperature and suction filtered. The filtrate is concentrated in vacuo and the residue dissolved in 250 parts of methanol. After the addition of 100 parts of water and treatment of the solution with activated carbon, crystallization is induced by cooling. The mush of crystals is suction filtered, washed with 50% aqueous methanol and dried in vacuo. The melting point of the crude product is 125° to 128°C. Pure 2,3-dihydro-3,3-dimethyl-2-morpholinobenzofuran-5-ylmethylaminosulfonate is obtained by crystallization of a sample from 80% methanol. Melting point: 129° to 131°C.

The compound has the following structural formula:

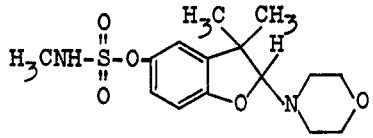

The following compounds are prepared analogously:
2,3-dihydro-3,3-dimethyl-2-morpholinobenzofuran-5-ylaminosulfonate,
2,3-dihydro-3,3-dimethyl-2-morpholinobenzofuran-5-ylethylaminosulfonate, m.p. 95° to 97°C,
2,3-dihydro-3,3-dimethyl-2-morpholinobenzofuran-5-ylpropylaminosulfonate, non-distillable oil,
2,3-dihydro-3,3-dimethyl-2-morpholinobenzofuran-5-ylisopropylaminosulfonate, m.p. 117° to 119°C,
2,3-dihydro-3,3-dimethyl-2-morpholinobenzofuran-5-ylbutylaminosulfonate, 2,3-dihydro-3,3-dimethyl-2-morpholinobenzofuran-5-yl-β-chloroethylaminosulfonate,
2,3-dihydro-3,3-dimethyl-2-piperidinobenzofuran-5-ylaminosulfonate,
2,3-dihydro-3,3-dimethyl-2-piperidinobenzofuran-5-ylmethylaminosulfonate,
2,3-dihydro-3,3-dimethyl-2-piperidinobenzofuran-5-ylethylaminosulfonate,
2,3-dihydro-3,3-dimethyl-2-piperidinobenzofuran-5-ylpropylaminosulfonate,
2,3-dihydro-3,3-dimethyl-2-piperidinobenzofuran-5-ylisopropylaminosulfonate,
2,3-dihydro-3,3-dimethyl-2-piperidinobenzofuran-5-yl-β-chloroethylaminosulfonate,
2,3-dihydro-3,3-dimethyl-2-(4-methylpiperazino)-benzofuran-5-ylaminosulfonate,
2,3-dihydro-3,3-dimethyl-2-(4-methylpiperazino)-benzofuran-5-ylmethylaminosulfonate,
2,3-dihydro-3,3-dimethyl-2-(4-methylpiperazino)-benzofuran-5-ylethylaminosulfonate,
2,3-dihydro-3,3-dimethyl-2-(4-methylpiperazino)-benzofuran-5-ylpropylaminosulfonate,
2,3-dihydro-3,3-dimethyl-2-(4-methylpiperazino)-benzofuran-5-ylisopropylaminosulfonate,
2,3-dihydro-3,3-dimethyl-2-(hexamethylenimino)-benzofuran-5-ylmethylaminosulfonate,
2,3-dihydro-3,3-dimethyl-2-(hexamethylenimino)-benzofuran-5-ylethylaminosulfonate,
2,3-dihydro-3-ethyl-2-morpholinobenzofuran-5-yl-methylaminosulfonate,
2,3-dihydro-3-ethyl-2-piperidinobenzofuran-5-yl-methylaminosulfonate, m.p. 114° to 115°C,
2,3-dihydro-3-ethyl-2-pyrrolidinobenzofuran-5-yl-methylaminosulfonate,
2,3-dihydro-3,3-dimethyl-2-(dimethylamino)-benzofuran-5-yl-methylaminosulfonate,
2,3-dihydro-3,3-dimethyl-2-(dimethylamino)-benzofuran-5-yl-ethylaminosulfonate,
2,3-dihydro-3,3,6-trimethyl-2-morpholinobenzofuran-5-ylmethylaminosulfonate,
2,3-dihydro-3,3,6-trimethyl-2-morpholinobenzofuran-5-ylethylaminosulfonate,
2,3-dihydro-3,3,6,7-tetramethyl-2-morpholinobenzofuran-5-yl-methylaminosulfonate,
2,3-dihydro-3,3,6,7-tetramethyl-2-morpholinobenzofuran-5-yl-ethylaminosulfonate,
2,3-dihydro-3,3-dimethyl-2-pyrrolidino-4,6-dichlorobenzofuran-5-ylmethylaminosulfonate,
2,3-dihydro-3,3-dimethyl-2-morpholino-6-chlorobenzofuran-5-yl-methylaminosulfonate,
2,3-dihydro-3,3-dimethyl-2-morpholino-4,6-dichlorobenzofuran-5-ylmethylaminosulfonate,
2,3-dihydro-3,3-dimethyl-2-morpholino-4-acetylbenzofuran-5-yl-methylaminosulfonate,
2,3-dihydro-3,3-dimethyl-2-morpholino-6-methoxybenzofuran-5-ylmethylaminosulfonate,
2,3-dihydro-2,3-tetramethylene-2-morpholinobenzofuran-5-ylmethylaminosulfonate,
2,3-dihydro-2,3-trimethylene-2-morpholinobenzofuran-5-ylmethylaminosulfonate.

EXAMPLE 2

At 20° to 30°C, a solution of 99.6 parts of 2,3-dihydro-3,3-dimethyl-2-morpholino-5-hydroxybenzofuran in 360 parts of tetrahydrofuran is added, while stirring and as hydrogen is evolved, to a suspension of 9.6 parts of sodium hydride in 190 parts of tetrahydrofuran. To complete the reaction the mixture is stirred for 1 hour at 40°C. Subsequently, 60 parts of dimethylaminosulfonyl chloride is dripped into the reaction mixture at 30° to 35°C and the reaction brought to completion within a period of 30 minutes at 50° to 55°C. The sodium chloride is separated, the clear solution is concentrated in vacuo, the residue is dissolved with heating in methanol and the hot solution is filtered. The crystals are cooled and subjected to suction filtration. The melting point of the crude product is 110° to 113°C. Recrystallization from methanol gives pure 2,3-dihydro-3,3-dimethyl-2-morpholinobenzofuran-5-yldimethylaminosulfonate melting at 113° to 114°C.

The compound has the following structural formula:

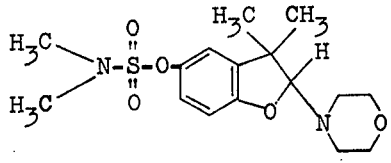

The following compounds were prepared analogously:
2,3-dihydro-3,3-dimethyl-2-morpholinobenzofuran-5-yldiethylaminosulfonate, m.p. 90° to 92°C,
2,3-dihydro-3,3-dimethyl-2-morpholinobenzofuran-5-yl-N-methyl-β-chloroethylaminosulfonate,
2,3-dihydro-3,3-dimethyl-2-piperidinobenzofuran-5-yldimethylaminosulfonate,
2,3-dihydro-3,3-dimethyl-2-piperidinobenzofuran-5-yldiethylaminosulfonate,
2,3-dihydro-3,3-dimethyl-2-pyrrolidinobenzofuran-5-yldimethylaminosulfonate,
2,3-dihydro-3,3-dimethyl-2-pyrrolidinobenzofuran-5-yldiethylaminosulfonate,
2,3-dihydro-3-ethyl-2-piperidinobenzofuran-5-yldimethylaminosulfonate,
2,3-dihydro-3-ethyl-2-piperidinobenzofuran-5-yldiethylaminosulfonate,
2,3-dihydro-3,3-dimethyl-2-morpholinobenzofuran-5-yl-N-methylethylaminosulfonate.

The preparation of the substituted 5-hydroxybenzofuran derivatives used as starting materials is known for instance from Dutch Pat. No. 6,512,311, U.S. Pat. No. 3,184,457 and J. Prakt. Chem., 4th series, vol. 32, page 144 (1966).

EXAMPLE 3

At 80°C and while stirring, 68 parts of 2,3-dihydro-3,3-dimethyl-2-morpholinobenzofuranyl-5-methylaminosulfonate is added all at once to a mixture of 133 parts of water and 68 parts of concentrated hydrochloric acid. The mixture is heated rapidly to 90° to 95°C and kept for 2 minutes at this temperature. The reaction solution is then immediately cooled by adding ice. Extraction is carried out with ether, and the ether solution is washed twice with water, dried with magnesium sulfate and concentrated in vacuo. The viscous residue is dissolved in 100 parts of ether, 60 parts of n-hexane is added and, after cooling, crystals of 2,3-dihydro-3,3-dimethyl-2-hydroxybenzofuran-5-ylmethylaminosulfonate are obtained; m.p. 111° to 112°C.

The compound has the following structural formula:

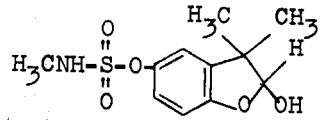

The following compounds were obtained analogously:

2,3-dihydro-3,3-dimethyl-2-hydroxybenzofuran-5-ylethylaminosulfonate, $n_D^{25} = 1.5250$,
2,3-dihydro-3,3-dimethyl-2-hydroxybenzofuran-5-ylpropylaminosulfonate,
2,3-dihydro-3,3-dimethyl-2-hydroxybenzofuran-5-ylisopropylaminosulfonate, m.p. 75° to 76°C,
2,3-dihydro-3,3-dimethyl-2-hydroxybenzofuran-5-ylbutylaminosulfonate,
2,3-dihydro-3,3-dimethyl-2-hydroxybenzofuran-5-yl-β-chloroethylaminosulfonate,
2,3-dihydro-3,3-dimethyl-2-hydroxybenzofuran-5-yldimethylaminosulfonate, m.p. 90° to 91°C,
2,3-dihydro-3,3-dimethyl-2-hydroxybenzofuran-5-yldiethylaminosulfonate, m.p. 65° to 66°C,
2,3-dihydro-3,3-dimethyl-2-hydroxybenzofuran-5-ylaminosulfonate,
2,3-dihydro-3,3-dimethyl-2-hydroxybenzofuran-5-yl-N-methyl-N-β-chloroethylaminosulfonate,
2,3-dihydro-3-ethyl-2-hydroxybenzofuran-5-ylmethylaminosulfonate,
2,3-dihydro-3,3,6,7-tetramethyl-2-hydroxybenzofuran-5-ylmethylaminosulfonate,
2,3-dihydro-3,3,6,7-tetramethyl-2-hydroxybenzofuran-5-ylethylaminosulfonate.

EXAMPLE 4

4 drops of concentrated sulfuric acid are added to a solution of 22.5 parts of 2,3-dihydro-3,3-dimethyl-2-hydroxybenzofuran-5-ylmethylaminosulfonate in 200 parts of methanol. The mixture is then boiled under reflux for 30 minutes, cooled, neutralized with triethylamine and concentrated to dryness in vacuo. Treatment of the viscous residue with a mixture of ether and n-hexane gives crystals of 2,3-dihydro-3,3-dimethyl-2-methoxybenzofuran-5-ylmethylaminosulfonate; m.p. 89° to 91°C.

The compound has the following structural formula:

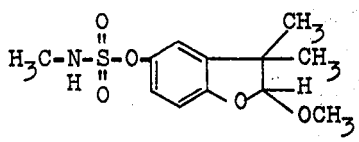

The following compounds were prepared analogously:
2,3-dihydro-3,3-dimethyl-2-ethoxybenzofuran-5-ylmethylaminosulfonate, m.p. 64° to 66°C,
2,3-dihydro-3,3-dimethyl-2-propoxybenzofuran-5-ylmethylaminosulfonate, m.p. 51° to 53°C,
2,3-dihydro-3,3-dimethyl-2-isopropoxybenzofuran-5-ylmethylaminosulfonate, m.p. 58° to 59°C,
2,3-dihydro-3,3-dimethyl-2-butoxybenzofuran-5-ylmethylaminosulfonate,
2,3-dihydro-3,3-dimethyl-2-allyloxybenzofuran-5-ylmethylaminosulfonate, m.p. 66° to 67.5°C,
2,3-dihydro-3,3-dimethyl-2-propargyloxybenzofuran-5-ylmethylaminosulfonate, m.p. 70° to 71°C,
2,3-dihydro-3,3-dimethyl-2-(2-chloroethoxy)-benzofuran-5-ylmethylaminosulfonate, m.p. 52° to 54°C,
2,3-dihydro-3,3-dimethyl-2-(2-methoxyethoxy)-benzofuran-5-ylmethylaminosulfonate,
2,3-dihydro-3,3-dimethyl-2-ethylthiobenzofuran-5-ylmethylaminosulfonate,
2,3-dihydro-3,3-dimethyl-2-methoxybenzofuran-5-ylethylaminosulfonate, $n_D^{25} = 1.5130$,
2,3-dihydro-3,3-dimethyl-2-ethoxybenzofuran-5-ylethylaminosulfonate, $n_D^{25} = 1.5065$,
2,3-dihydro-3,3-dimethyl-2-propoxybenzofuran-5-ylethylaminosulfonate, $n_D^{25} = 1.5005$,
2,3-dihydro-3,3-dimethyl-2-isopropoxybenzofuran-5-ylethylaminosulfonate, $n_D^{25} = 1.5020$,
2,3-dihydro-3,3-dimethyl-2-allyloxybenzofuran-5-ylethylaminosulfonate,
2,3-dihydro-3,3-dimethyl-2-methoxybenzofuran-5-ylpropylaminosulfonate, m.p. 74° to 75°C,
2,3-dihydro-3,3-dimethyl-2-ethoxybenzofuran-5-ylpropylaminosulfonate, m.p. 49° to 50°C,
2,3-dihydro-3,3-dimethyl-2-propopxybenzofuran-5-ylpropylaminosulfonate, m.p. 54° to 55°C,
2,3-dihydro-3,3-dimethyl-2-isopropoxybenzofuran-5-ylpropylaminosulfonate, m.p. 79° to 81°C,
2,3-dihydro-3,3-dimethyl-2-allyloxybenzofuran-5-ylpropylaminosulfonate,
2,3-dihydro-3,3-dimethyl-2-methoxybenzofuran-5-ylisopropylaminosulfonate, m.p. 84° to 86°C,
2,3-dihydro-3,3-dimethyl-2-ethoxybenzofuran-5-ylisopropylaminosulfonate, m.p. 73° to 74°C,
2,3-dihydro-3,3-dimethyl-2-propoxybenzofuran-5-ylisopropylaminosulfonate, m.p. 77° to 78°C,
2,3-dihydro-3,3-dimethyl-2-isopropoxybenzofuran-5-ylisopropylaminosulfonate, m.p. 69° to 70°C,
2,3-dihydro-3,3-dimethyl-2-allyloxybenzofuran-5-ylisopropylaminosulfonate,
2,3-dihydro-3,3-dimethyl-2-methoxybenzofuran-5-yldimethylaminosulfonate, $n_D^{25} = 1.5087$, b.p. (0.01 mm): 147° to 150°C,
2,3-dihydro-3,3-dimethyl-2-ethoxybenzofuran-5-yldimethylaminosulfonate, $n_D^{20} = 1.5023$, b.p. (0.01 mm): 165° to 167°C,
2,3-dihydro-3,3-dimethyl-2-propoxybenzofuran-5-yldimethylaminosulfonate, $n_D^{25} = 1.5002$, b.p. (0.01 mm): 170° to 173°C,
2,3-dihydro-3,3-dimethyl-2-isopropoxybenzofuran-5-yldimethylaminosulfonate, m.p. 37° to 38°C,
2,3-dihydro-3,3-dimethyl-2-allyloxybenzofuran-5-yldimethylaminosulfonate, b.p. (0.05 mm): 161°C, $n_D^{25} = 1.5125$,
2,3-dihydro-3,3-dimethyl-2-methoxybenzofuran-5-yldiethylaminosulfonate, m.p. 52° to 53°C,
2,3-dihydro-3,3-dimethyl-2-ethoxybenzofuran-5-yldiethylaminosulfonate, $n_D^{25} = 1.4995$,
2,3-dihydro-3,3-dimethyl-2-propoxybenzofuran-5-yldiethylaminosulfonate,
2,3-dihydro-3,3-dimethyl-2-isopropoxybenzofuran-5-yldiethylaminosulfonate,
2,3-dihydro-3,3-dimethyl-2-allyloxybenzofuran-5-yldiethylaminosulfonate, $n_D^{25} = 1.5050$,
2,3-dihydro-3,3-dimethyl-2-(2-chloroethoxy)-benzofuran-5-yldimethylaminosulfonate, b.p. (0.05 mm): 170° to 173°C, $n_D^{25} = 1.5135$,
2,3-dihydro-3,3-dimethyl-2-methoxyethoxybenzofuran-5-yldimethylaminosulfonate, b.p. (0.05 mm): 168° to 172°C, $n_D^{25} = 1.5025$,
2,3-dihydro-3,3-dimethyl-2-methoxybenzofuran-5-yl-N-methylethylaminosulfonate, b.p. (0.05 mm): 143° to 152°C, $n_D^{25} = 1.5075$,
2,3-dihydro-3,3-dimethyl-2-ethoxybenzofuran-5-yl-N-methylethylaminosulfonate,
2,3-dihydro-3,3-dimethyl-2-propoxybenzofuran-5-yl-N-methylethylaminosulfonate,
2,3-dihydro-3,3-dimethyl-2-isopropoxybenzofuran-5-yl-N-methylethylaminosulfonate, 2,3-dihydro-3,3-dimethyl-2-methoxybenzofuran-5-yl-N-methyl-β-chloroethylaminosulfonate,
2,3-dihydro-3,3-dimethyl-2-ethoxybenzofuran-5-yl-N-methyl-β-chloroethylaminosulfonate,
2,3-dihydro-3,3-dimethyl-2-propoxybenzofuran-5-yl-N-methyl-β-chloroethylaminosulfonate,
2,3-dihydro-3,3-dimethyl-2-isopropoxybenzofuran-5-yl-N-methyl-β-chloroethylaminosulfonate,
2,3-dihydro-3,3-dimethyl-2-methoxybenzofuran-5-ylaminosulfonate, m.p. 130° to 131°C,
2,3-dihydro-3,3-dimethyl-2-ethoxybenzofuran-5-ylaminosulfonate, m.p. 139° to 140°C,
2,3-dihydro-3,3-dimethyl-2-propoxybenzofuran-5-ylaminosulfonate,
2,3-dihydro-3,3-dimethyl-2-isopropoxybenzofuran-5-ylaminosulfonate,
2,3-dihydro-3,3-dimethyl-2-allyloxybenzofuran-5-ylaminosulfonate,
2,3-dihydro-3,3,6,7-tetramethyl-2-ethoxybenzofuran-5-ylmethylaminosulfonate,
2,3-dihydro-3,3-dimethyl-2-methylcarbonyloxybenzofuran-5-yldimethylaminosulfonate, m.p. 66° to 68°C,
2,3-dihydro-3,3-dimethyl-2-chloromethylcarbonyloxybenzofuran-5-yldimethylaminosulfonate, m.p. 89° to 90°C,
2,3-dihydro-3,3-dimethyl-2-ethylcarbonyloxybenzofuran-5-yldimethylaminosulfonate, m.p. 53° to 55°C,
2,3-dihydro-3,3-dimethyl-2-methoxycarbonyloxybenzofuran-5-yldimethylaminosulfonate, m.p. 101° to 102°C,
2,3-dihydro-3,3-dimethyl-2-ethoxycarbonyloxybenzofuran-5-yldimethylaminosulfonate,
2,3-dihydro-3,3-dimethyl-2-methylcarbamoyloxybenzofuran-5-yldimethylaminosulfonate, m.p. 100° to 102°C,
2,3-dihydro-3,3-dimethyl-2-ethylcarbamoyloxybenzofuran-5-yldimethylaminosulfonate, m.p. 111° to 113°C,
2,3-dihydro-3,3-dimethyl-2-isopropylcarbamoyloxybenzofuran-5-yldimethylaminosulfonate, m.p. 107° to 109°C,
2,3-dihydro-3,3-dimethyl-2-chloromethylcarbonyloxybenzofuran-5-yldiethylaminosulfonate, non-distillable oil, $n_D^{25} = 1.5078$,
2,3-dihydro-3,3-dimethyl-2-methoxycarbonyloxybenzofuran-5-yldiethylaminosulfonate, m.p. 96° to 97°C,
2,3-dihydro-3,3-dimethyl-2-methylcarbamoyloxybenzofuran-5-yldiethylaminosulfonate, m.p. 122° to 123°C,
2,3-dihydro-3,3-dimethyl-2-ethylcarbamoyloxybenzofuran-5-yldiethylaminosulfonate, m.p. 125° to 126°C.

The new active ingredients have a strong herbicidal effect and may therefore be used as weedicides or for controlling unwanted plants. Whether the new active ingredients are used as total or selective agents depends in essence on the amount of ingredient used per unit area.

By weeds and unwanted plant growth are meant all monocotyeldonous and dicotyledonous plants which grow in loci where they are not desired.

The agents according to the invention may therefore be used for controlling for instance Gramineae, such as Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
Cyperaceae, such as
 Carex spp.
 Cyperus spp.
 Scirpus spp.
dicotyledonous weeds, such as
Malvaceae, e.g.,
 Abutilon theoprasti
 Sida spp.
 Malva spp.
Compositae, such as
 Ambrosia spp.
 Lactuca spp.
 Senecio spp.
 Sonchus spp.
 Xanthium spp.
 Iva spp.
 Galinsoga spp.
 Taraxacum spp.
 Chrysanthemum spp.
 Bidens spp.
 Cirisum spp.
Convolvulaceae, such as
 Convolvulus spp.
 Ipomoea spp.
 Jaquemontia tamnifolia
Cruciferae, such as
 Barbarea vulgaris
 Brassica spp.
 Capsella spp.
 Sisymbrium spp.
 Thlaspi spp.
 Sinapis arvensis
 Raphanus spp.
Geraniaceae, such as
 Erodium spp.
 Geranium spp.
Portulacaceae, such as
 Portulaca spp.
Primulaceae, such as
 Anagallis arvensis
 Lysimachia spp.
Rubiaceae, such as
 Richardia spp.
 Galium spp.
Scrophulariaceae, such as
 Linaria spp.
 Veronica spp.
Solanaceae, such as
 Physalis spp.
 Solanum spp.
 Datura spp.
Urticaceae, such as
 Urtica spp.
Violaceae, such as
 Viola spp.
Zygophyllaceae, such as
 Tribulus terrestis
Euphorbiaceae, such as
 Mercurialis annua
Umbelliferae, such as
 Daucus carota
 Aethusa cynapium
Commelinaceae, such as
 Commelina spp.
Labiatae, such as
 Lamium spp.
 Galeopsis spp.
Leguminosae, such as
 Medicago spp.
 Trifolium spp.
 Vicia spp.
 Lathyrus spp.
Plantaginaceae, such as
 Plantago spp.
Polygonaceae, such as
 Polygonum spp.
 Rumex spp.
Aizoaceae, such as
 Mollugo verticillata
Amaranthaceae, such as
 Amaranthus spp.
Boraginaceae, such as
 Amsinckia spp.

Dactylis spp.
Avena spp.
Bromus spp.
Uniola spp.
Poa spp.
Leptochloa spp.
Brachiaria spp.
Eleusine spp.
Cenchrus spp.
Eragrostis spp.
etc.;

Eleocharis spp.
etc.;

Hibiscus spp.
etc.;

Centaurea spp.
Tussilago spp.
Lapsana communis
Tagetes spp.
Erigeron spp.
Anthemis spp.
Matricaria spp.
Artemisia spp.
etc.;

Cuscuta spp.
etc.;

Arabidopsis thaliana
Descurainia spp.
Draba spp.
Coronopus didymus
Lepidium spp.
etc.;

etc.;

etc.;

etc.;

Diodia spp.
etc.;

Digitalis spp.
etc.;

Nicandra spp.
etc.;

etc.;

etc.;

etc.;

Euphorbia spp.

Ammi majus
etc.;

etc.;

etc.;

Sesbania exaltata
Cassia spp.
etc.;

etc.;

Fagopyrum spp.
etc.;

etc.;

etc.;

Anchusa spp.

-continued

| | |
|---|---|
| Myostis spp. | etc.; |
| Lithospermum spp. | |
| Caryophyllaceae, such as | |
| Stellaria spp. | Silene spp. |
| Spergula spp. | Cerastium spp. |
| Saponaria spp. | Agrostemma githago |
| Scleranthus annuus | etc.; |
| Chenopodiaceae, such as | |
| Chenopodium spp. | Atriplex spp. |
| Kochia spp. | Monolepsis nuttaliana |
| Salsola kali | etc.; |
| Lythraceae, such as | |
| Cuphea spp. | etc.; |
| Oxalidaceae, such as | |
| Oxalis spp. | etc.; |
| Ranunculaceae, such as | |
| Ranunculus spp. | Adonis spp. |
| Delphinium spp. | etc.; |
| Papaveraceae, such as | |
| Papaver spp. | etc.; |
| Fumaria officinalis | |
| Onagraceae, such as | |
| Jussiaea spp. | etc.; |
| Rosaceae, such as | |
| Alchemillia spp. | etc.; |
| Potentilla spp. | |
| Potamogetonaceae, such as | |
| Potamogeton spp. | etc.; |
| Najadaceae, such as | |
| Najas spp. | etc.; |
| Marsileaceae, such as | |
| Marsilea quadrifolia | etc. |

The amount used of the agents of the invention may vary and depends on the effect desired; it generally is from 0.1 to 15 or more, and preferably from 0.2 to 6, kg per hectare. The new agents may be employed in cereal crops, such as

| | |
|---|---|
| Avena spp. | Sorghum |
| Triticum spp. | Zea mays |
| Hordeum spp. | Panicum miliaceum |
| Secale spp. | Oryza spp. |
| and in dicotyledon crops, such as | |
| Cruciferae, e.g. | |
| Brassica spp. | Raphanus spp. |
| Sinapis spp. | Lepidium spp. |
| Compositae, e.g. | |
| Lactuca spp. | Carthamus spp. |
| Helianthus spp. | Scorzonera spp. |
| Malvaceae, e.g. | |
| Gossypium hirsutum | |
| Leguminosae, e.g. | |
| Medicago spp. | Phaseolus spp. |
| Trifolium spp. | Arachis spp. |
| Pisum spp. | Glycine max. |
| Chenopodiaceae, e.g. | |
| Beta vulgaris | |
| Spinacia spp. | |
| Solanaceae, e.g. | |
| Solanum spp. | Capsicum annuum |
| Nicotiania spp. | |
| Linaceae, e.g. | |
| Linum spp. | |
| Umbelliferae, e.g. | |
| Petroselinum spp. | Apium graveolens, |
| Daucus carota | |
| Rosaceae, e.g. | |
| Fragaria | |
| Cucurbitaceae, e.g. | |
| Cucumis spp. | Cucurbita spp. |
| Liliaceae, e.g. | |
| Allium spp. | |
| Vitaceae, e.g. | |
| Vitis vinifera | |
| Bromeliaceae, e.g. | |
| Ananas sativus. | |

Application may be effected for instance in the form of directly sprayable solutions, powders, suspensions, dispersions, emulsions, oil dispersions, pastes, dusts or granules by spraying, atomizing, dusting, scattering or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone and water, are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkdyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders and dusts may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, preferably from 0.5 to 90, % by weight of active ingredient.

There may be added to the compositions or individual active ingredients (used singly, either before, simultaneously with and/or after the active ingredients of the invention) oils of various types, herbicides, fungicides, nematocides, insecticides, bactericides, trace elements, fertilizers, antifoams (e.g., silicones) growth regulators, antidotes and other herbicidally effective compounds such as substituted anilines, substituted aryloxycarboxylic acids and salts, esters and amides thereof,
substituted ethers,
substituted arsonic acids and their salts, esters and amides,
substituted benzimidazoles,
substituted benzisothiazoles,
substituted benzothiadiazionone dioxides,
substituted benzoxazines,
substituted benzoxazinones,
substituted benzothiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkylthiol- or -dithiophosphates,
substituted quinazolines,
substituted cycloalkylamidocarbothiolic acids and their salts, esters and amides,
substituted cycloalkylcarbonamidothiazoles,
substituted dicarboxylic acids and their salts, esters and amides,
substituted dihydrobenzofuranyl sulfonates,
substituted disulfides,
substituted dipyridylium salts,
substituted dithiocarbamates,
substituted dithiophosphoric acids and their salts, esters and amides,
substituted ureas,
substituted hexahydro-1-H-carbothioates,
substituted hydantoins,
substituted hydrazides,
substituted hydrazonium salts,
substituted isooxazole pyrimidones,
substituted imidazoles,
substituted isothiazole pyrimidones,
substituted ketones,
substituted naphthoquinones,
substituted aliphatic nitriles,
substituted aromatic nitriles,
substituted oxadiazoles,
substituted oxadiazinones,
substituted oxadiazolidine diones,
substituted oxadiazine diones,
substituted phenols and their salts and esters,
substituted phosphonic acids and their salts, esters and amides,
substituted phosphonium chlorides,
substituted phosphonalkylglycines,
substituted phosphites,
substituted phosphoric acids and their salts, esters and amides,
substituted piperidines,
substituted pyrazoles,
substituted pyrazole alkylcarboxylic acids and their salts, esters and amides,
substituted pyrazolium salts,
substituted pyrazolium alkyl sulfates,
substituted pyridazines,
substituted pyridazones,
substituted pyridine carboxylic acids and their salts, esters and amides,
substituted pyridines,
substituted pyridine carboxylates,
substituted pyridinones,
substituted pyrimidines,
substituted pyrimidones,
substituted pyrrolidine carboxylic acid and its salts, esters and amides,
substituted pyrrolidines,
substituted pyrrolidones,
substituted arylsulfonic acids and their salts, esters and amides,
substituted styrenes,
substituted tetrahydrooxadiazine diones,
substituted tetrahydrooxadiazole diones,
substituted tetrahydromethanoindenes,
substituted tetrahydrooxadiazole thiones,
substituted tetrahydrodiazine thiones,
substituted tetrahydrothiadiazole diones,
substituted aromatic thiocarbonylamides,
substituted thiocarboxylic acids and their salts, esters and amides,
substituted thiol carbamates,
substituted thioureas,
substituted thiophosphoric acids and their salts, esters and amides,
substituted triazines,
substituted triazoles,
substituted uracils,
substituted uretidine diones.

These agents (either one or several from the same or different groups of substances) may be added to the herbicides according to the invention in a ratio by weight of from 1 : 10 to 10 : 1. The same applies to oils, fungicides, nematocides, insecticides, bactericides, trace elements, fertilizers, antidotes and growth regulators.

The agents according to the invention may be applied either once or several times before or after planting, before sowing, pre- or postemergence, or during emergence of the crop plants or weeds, and used with an ultra-low volume of water or as a tankmix in the case of mixtures.

EXAMPLE 5

In the greenhouse, loamy sandy soil is filled into pots and sown with *Beta vulgaris, Spinacia oleracea, Avena fatua, Echinochloa crus-galli, Lolium multiflorum, Poa annua* and *Sinapis arvensis*. The soil prepared in this manner is then immediately treated with 2 kg per hectare of each of the following compounds, each being dispersed or emulsified in 500 liters of water per hectare:

I 2,3-dihydro- 3,3-dimethyl-2-methoxybenzofuran-5-ylethylaminousulfonate,

II 2,3-dihydro-3,3-dimethyl-2-methoxybenzofuran-5-ylmethylaminosulfonate,

III 2,3-dihydro-3,3-dimethyl-2-isopropoxybenzofuran-5-ylmethylaminosulfonate,

IV 2,3-dihydro-3,3-dimethyl-2-morpholinobenzofuran-5-ylmethylaminosulfonate,

V 2,3-dihydro-3,3-dimethyl- 2-ethoxybenzofuran-5-ylmethylaminosulfonate,

VI 2,3-dihydro-3,3-dimethyl-2-ethoxybenzofuran-5-ylethylaminosulfonate,

VII 2,3-dihydro-3,3-dimethyl-2-isopropoxybenzofuran-5-ylethylaminosulfonate,

VIII 2,3-dihydro-3,3-dimethyl-2-morpholinobenzofuran-5-yldimethylaminosulfonate, X 2,3-dihydro-3,3-dimethyl-2-hydroxybenzofuran-5-yldiethylaminosulfonate, XI 2,3-dihydro-3,3-dimethyl-2-methoxybenzofuran-5-ylmethylethylaminosulfonate, XII 2,3-dihydro-3,3-dimethyl-2-β-chloroethoxybenzofuran-5-yldimethylaminosulfonate, XIII 2,3-dihydro-3,3-dimethyl-2-β-methoxyethoxybenzofuran-5-yldimethylaminosulfonate, XIV 2,3-dihydro-3,3-dimethyl-2-allyloxybenzofuran-5-yldimethylaminosulfonate, XV 2,3-dihydro-3,3-dimethyl-2-β-chloroethoxybenzofuran-5-ylmethylaminosulfonate, XVI 2,3-dihydro-3,3-dimethyl-2-propoxybenzofuran-5-ylmethylaminosulfonate, XVII 2,3-dihydro-3,3-dimethyl-2-allyloxybenzofuran-5-ylmethylaminosulfonate, XVIII 2,3-dihydro-3,3-dimethyl-2-propargyloxybenzofuran-5-ylmethylaminosulfonate IX 2,3-dihydro-3,3-dimethyl-2-ethoxybenzofuran-5-ylmethanesulfonate (prior art compound used for comparison purposes).

After 3 to 4 weeks it is ascertained that active ingredients I to VIII and X to XVIII have a better herbicidal action then IX, combined with superior crop plant compatibility.

The results are given below:

III 2,3-dihydro-3,3-dimethyl-2-methoxybenzofuran-5-ylethylaminosulfonate,

IV 2,3-dihydro-3,3-dimethyl-2-morpholinobenzofuran-5-ylmethylaminosulfonate,

V 2,3-dihydro-3,3-dimethyl-2-isopropoxybenzofuran-5-ylmethylaminosulfonate,

VI 2,3-dihydro-3,3-dimethyl-2-isopropoxybenzofuran-5-ylethylaminosulfonate,

VII 2,3-dihydro-3,3-dimethyl-2-morpholinobenzofuran-5-yldimethylaminosulfonate,

IX 2,3-dihydro-3,3-dimethyl-2-hydroxybenzofuran-5-yldiethylaminosulfonate,

X 2,3-dihydro-3,3-dimethyl-2-methoxybenzofuran-5-ylmethylethylaminosulfonate,

XI 2,3-dihydro-3,3-dimethyl-2-β-chloroethoxybenzofuran-5-yldimethylaminosulfonate, XII 2,3-dihydro-3,3-dimethyl-2-β-methoxyethoxybenzofuran-5-yldimethylaminosulfonate, XIII 2,3-dihydro-3,3-dimethyl-2-allyloxybenzofuran-5-yldimethylaminosulfonate, XIV 2,3-dihydro-3,3-dimethyl-2-β-chloroethoxybenzofuran-5-ylmethylaminosulfonate, XV 2,3-dihydro-3,3-dimethyl-2-propoxybenzofuran-5-ylmethylaminosulfonate,

| Active ingredient kg/ha | I 2 | II 2 | III 2 | IV 2 | V 2 | VI 2 | VII 2 |
|---|---|---|---|---|---|---|---|
| Crop plants: | | | | | | | |
| Beta vulgaris | 0 | 0 | 0 | 0 | 0 | 5 | 0 |
| Spinacia oleracea | 0 | 0 | 0 | 0 | 0 | 10 | 2 |
| Unwanted plants: | | | | | | | |
| Avena fatua | 100 | 95 | 95 | 90 | 100 | 90 | 90 |
| Echinochloa crus-galli | 100 | 95 | 90 | 90 | 90 | 90 | 90 |
| Lolium multiflorum | 100 | 100 | 100 | 100 | 100 | 85 | 50 |
| Poa annua | 100 | 100 | 100 | 100 | 100 | 90 | 65 |
| Sinapis arvensis | 40 | 60 | 60 | 65 | 60 | 30 | 30 |

| Active ingredient kg/ha | VIII 2 | IX 2 | X 2 | XI 2 | XII 2 | XIII 2 | XIV 2 |
|---|---|---|---|---|---|---|---|
| Beta vulgaris | 0 | 10 | 0 | 0 | 0 | 0 | 0 |
| Spinacia oleracea | 0 | 15 | | | | | |
| Avena fatua | 85 | 80 | 100 | 90 | 85 | 95 | 90 |
| Echinochloa crus-galli | 85 | 80 | 100 | 100 | 90 | 85 | 90 |
| Lolium multiflorum | 100 | 80 | 100 | 90 | 100 | 80 | 90 |
| Poa annua | 95 | 85 | 100 | 90 | 100 | 85 | 90 |
| Sinapis arvensis | 30 | 20 | 80 | 30 | 30 | 30 | 30 |

| Active ingredient kg/ha | XV 2 | XVI 2 | XVII 2 | XVIII 2 |
|---|---|---|---|---|
| Beta vulgaris | 0 | 0 | 0 | 0 |
| Unwanted plants: | | | | |
| Avena fatua | 90 | 90 | 90 | 90 |
| Echinochloa crus-galli | 85 | 85 | 80 | 80 |
| Lolium multiflorum | 80 | 85 | 80 | 80 |
| Poa annua | 85 | 85 | 80 | 80 |
| Sinapis arvensis | 40 | 40 | 25 | 25 |

0 = no damage
100 = complete destruction

EXAMPLE 6

In the greenhouse, various plants are treated at a growth height of from 3 to 11 cm with 2 kg per hectare of each of the following active ingredients, each being dispersed or emulsified in 500 liters of water per hectare:

I 2,3-dihydro-3,3-dimethyl-2-ethoxybenzofuran-5-ylmethylaminosulfonate,

II 2,3-dihydro-3,3-dimethyl-2-methoxybenzofuran-5-ylmethylaminosulfonate,

XVI 2,3-dihydro-3,3-dimethyl-2-allyloxybenzofuran-5-ylmethylaminosulfonate,

XVII 2,3-dihydro-3,3-dimethyl-2-propargyloxybenzofuran-5-ylmethylaminosulfonate, VIII 2,3-dihydro-3,3-dimethyl-2-ethoxybenzofuran-5-ylmethanesulfonate (prior art compound used for comparison purposes).

After 2 to 3 weeks it is ascertained that active ingredients I to VII and IX to XVII have a better herbicidal action than VIII, combined with superior crop plant compatibility.

The results are given below:

| Active ingredient kg/ha | I 2 | II 2 | III 2 | IV 2 | V 2 | VI 2 | VII 2 |
|---|---|---|---|---|---|---|---|
| Crop plant: | | | | | | | |
| Beta vulgaris | 0 | 0 | 0 | 0 | 0 | 0 | 0 |
| Unwanted plants: | | | | | | | |
| Avena fatua | 100 | 100 | 100 | 85 | 85 | 90 | 90 |
| Echinochloa crus-galli | 100 | 100 | 100 | 80 | 80 | 85 | 90 |
| Poa annua | 95 | 95 | 100 | 85 | 80 | 85 | 85 |

| Active ingredient kg/ha | VIII 2 | IX 2 | X 2 | XI 2 | XII 2 | XIII 2 | XIV 2 |
|---|---|---|---|---|---|---|---|
| Crop plant: | | | | | | | |
| Beta vulgaris | 20 | 0 | 0 | 0 | 0 | 0 | 0 |
| Unwanted plants: | | | | | | | |
| Avena fatua | 75 | 75 | 80 | 85 | 90 | 90 | 100 |
| Echinochloa crus-galli | 70 | 80 | 80 | 75 | 70 | 75 | 90 |
| Poa annua | 70 | 85 | 80 | 80 | 70 | 80 | 70 |

| Active ingredient kg/ha | XV 2 | XVI 2 | XVII 2 |
|---|---|---|---|
| Crop plant: | | | |
| Beta vulgaris | 0 | 0 | 0 |
| Unwanted plants: | | | |
| Avena fatua | 90 | 95 | 90 |
| Echinochloa crus-galli | 80 | 80 | 70 |
| Poa annua | 85 | 95 | 70 |

0 = no damage
100 = complete destruction

The action of the following compounds corresponds to that of the compounds of the invention in Examples 5 and 6:

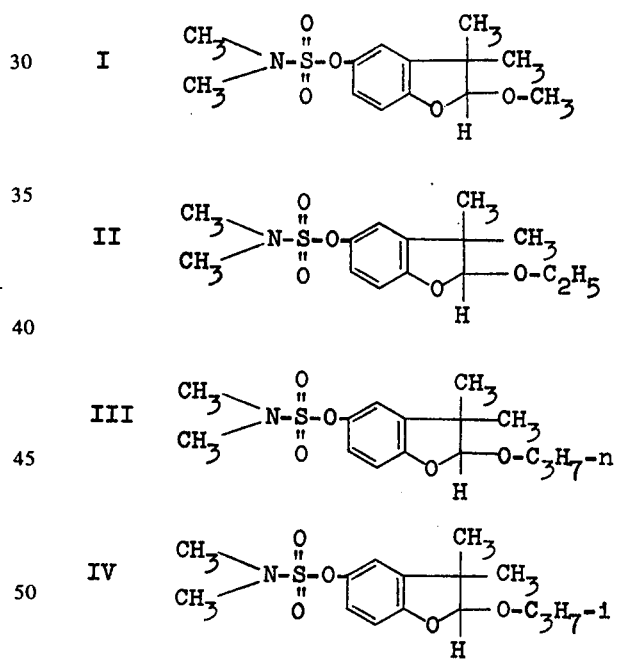

| $R^{10}$ | $R^6$ | $R^5$ |
|---|---|---|
| $-\underset{\underset{O}{\|}}{C}-CH_2-Cl$ | $-C_2H_5$ | $-C_2H_5$ |
| $-\underset{\underset{O}{\|}}{C}-CH_3$ | $-CH_3$ | $-CH_3$ |
| $-\underset{\underset{O}{\|}}{C}-CH_2Cl$ | $-CH_3$ | $-CH_3$ |
| $-\underset{\underset{O}{\|}}{C}-NH-CH_3$ | $-CH_3$ | $-CH_3$ |
| $-\underset{\underset{O}{\|}}{C}-NH-C_3H_7i$ | $-CH_3$ | $-CH_3$ |
| $-\underset{\underset{O}{\|}}{C}-NH-CH_3$ | $-C_2H_5$ | $-C_2H_5$ |
| $-\underset{\underset{O}{\|}}{C}-NH-C_2H_5$ | $-C_2H_5$ | $-C_2H_5$ |

EXAMPLE 7

In the greenhouse, loamy sandy soil is filled into pots and sown with the seeds of various plants. The soil prepared in this manner is immediately treated with 0.5 kg per hectare of each of the following compounds, each being dispersed or emulsified in 500 liters per hectare:

V   2-ethoxy-2,3-dihydro-3,3-dimethyl-5-benzofuranylmethanesulfonate (prior art compound used for comparison purposes).

After 3 to 4 weeks it is ascertained that active ingredients I to IV have a better herbicidal action than V, combined with superior crop plant compatibility.

The results are tabulated below:

| Active ingredient kg/ha | I 0.5 | II 0.5 | III 0.5 | IV 0.5 | V 0.5 |
|---|---|---|---|---|---|
| Beta vulgaris | 0 | 0 | .0 | 0 | 2.5 |
| Avena fatua | 100 | 100 | 80 | 90 | 16 |
| Lolium multiflorum | 80 | 85 | 50 | 60 | 4 |
| Echinochloa crus-galli | 100 | 100 | 50 | 100 | 25 |

-continued

| Active ingredient kg/ha | I 0.5 | II 0.5 | III 0.5 | IV 0.5 | V 0.5 |
|---|---|---|---|---|---|
| *Alopecurus myosuroides* | 90 | 90 | 80 | 85 | 17 |

0 = no damage
100 = complete destruction

The action of the following compounds corresponds to that of I and II in Example 7:

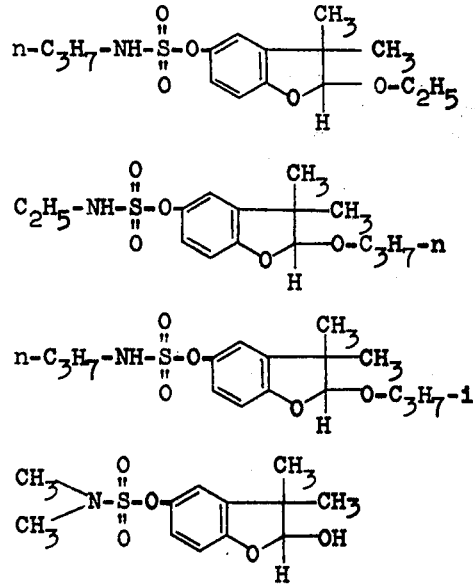

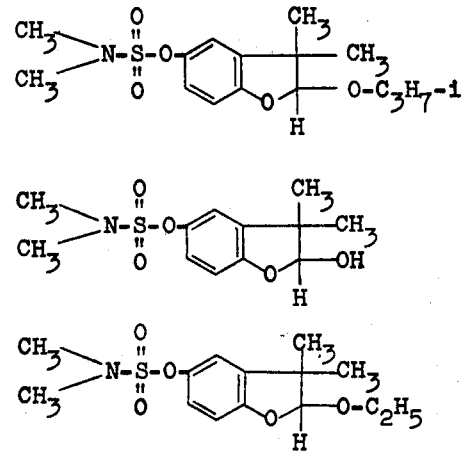

VI  2-ethoxy-2,3-dihydro-3,3-dimethyl-5-benzofuranylmethanesulfonate (prior art compound used for comparison purposes)

After 2 to 3 weeks it is ascertained that compounds I to V have a better herbicidal action than VI.

The results are given below:

| Active ingredient kg/ha | I 1 | II 1 | III 1 | IV 1 | V 1 | VI 1 |
|---|---|---|---|---|---|---|
| *Beta vulgaris* | 0 | 0 | 0 | 0 | 0 | 0 |
| *Avena fatua* | 100 | 80 | 90 | 90 | 100 | 55 |
| *Alopecurus myosuroides* | 85 | 80 | 85 | 80 | 85 | 50 |
| *Cynodon dactylon* | 85 | 80 | 80 | 80 | 85 | 50 |

0 = no damage
100 = complete destruction

The action of the following compounds corresponds to that of 1 to V in Example 8:

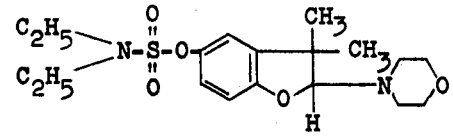

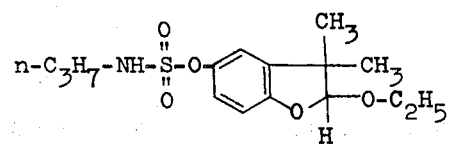

EXAMPLE 9

At −8° to −12°C and while stirring, 10.3 parts by weight of acetyl chloride is metered into a solution of 28.7 parts by weight of 2,3-dihydro-3,3-dimethyl-2-hydroxybenzofuran-5-yldimethylaminosulfonate and 14.1 parts by weight of triethylamine in 120 parts by

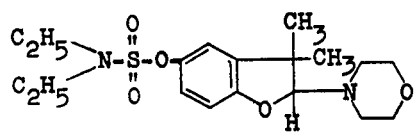

EXAMPLE 8

In the greenhouse, various plants are treated at a growth height of from 3 to 11 cm with 1 kg per hectare of each of the following active ingredients, each dispersed or emulsified in 500 liters of water per hectare:

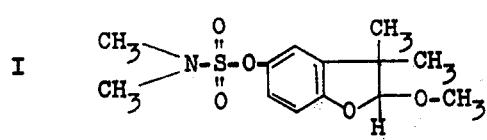

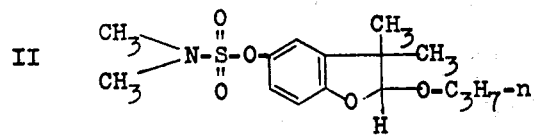

weight of (dry) ether. After one hour the reaction mixture is extracted three times with water. The organic phase is dried with magnesium sulfate and concentrated, whereupon most of the product is precipitated; m.p.: 66° to 68°C.

The compound has the following structural formula:

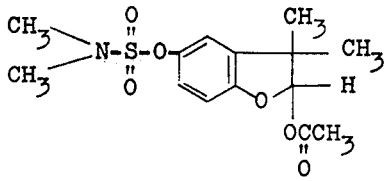

EXAMPLE 10

At −8° to −12°C and while stirring, 12.4 parts by weight of methyl chlorocarbonate is metered into a solution of 28.7 parts by weight of 2,3-dihydro-3,3-dimethyl-2-hydroxybenzofuran-5-yldimethylaminosulfonate and 14.1 parts by weight of -triethylamine in 120 parts of (dry) ether.

After working up as described in the foregoing example the reaction product is obtained as a crystalline substance; m.p.: 101° to 102°C.

The compound has the following structural formula:

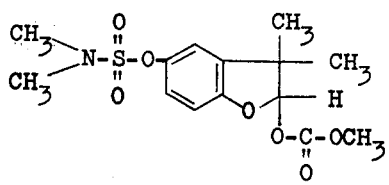

EXAMPLE 11

1 part by weight of triethylamine and then 6.9 parts by weight of methyl isocyanate are added to a solution of 28.7 parts by weight of 2,3-dihydro-3,3-dimethyl-2-hydroxybenzofuran-5-yldimethylaminosulfonate in 90 parts by weight of tetrahydrofuran. The mixture is left to stand at room temperature for 48 hours and then concentrated in vacuo. The residue is recrystallized from ether; m.p.: 100° to 102°C.

The compound has the following structural formula:

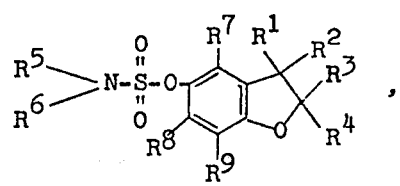

We claim:
1. A substituted benzofuranyl ester of the formula

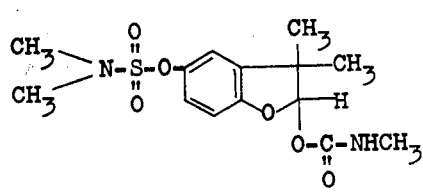

where $R^1$, $R^2$ and $R^3$ are identical or different and each denotes hydrogen or alkyl of 1 to 3 carbon atoms, or $R^1$ and $R^2$ together, or $R^2$ and $R^3$ together, denote alkylene of 2 to 5 carbon atoms, $R^4$ denotes hydroxy, alkoxy of 1 to 5 carbon atoms, alkenyloxy of 2 to 4 carbon atoms, alkynyloxy of 2 to 4 carbon atoms, methylmercapto, ethylmercapto, propylmercapto, benzylmercapto, β-phenylethylmercapto, p-chlorobenzylmercapto, phenoxy, nitrophenoxy, the group $OCOR^{12}$, where $R^{12}$ denotes alkyl of 1 to 4 carbon atoms, allyl, methallyl, propargyl, butynyl, phenyl, tolyl, chlorophenyl, nitrophenyl, methylamino, dimethylamino, methoxy, ethoxy, propoxy, allyloxy, chloroallyloxy, propargyloxy, chlorobutynyloxy, phenylamino, tolylamino, chlorophenylamino or phenoxy, tolyloxy and chlorophenyloxy, $R^5$ and $R^6$ are identical or different and each denotes hydrogen, alkyl of 1 to 4 carbon atoms and chloro substituted alkyl of 1 to 4 carbon atoms, and $R^7$, $R^8$ and $R^9$ are identical or different and each denotes hydrogen, methyl, ethyl, chloro, bromo, cyano, acetyl or methoxy.

2. The coumpound of claim 1 which is 2,3-dihydro-3,3-dimethyl-2-hydroxybenzofuran-5-ylmethylaminosulfonate.

3. The compound of claim 1 which is 2,3-dihydro-3,3-dimethyl-2-hydroxybenzofuran-5-ylethylaminosulfonate.

4. The compound of claim 1 which is 2,3-dihydro-3,3-dimethyl-2-hydroxybenzofuran-5-ylpropylaminosulfonate.

5. The compound of claim 1 which is 2,3-dihydro-3,3-dimethyl-2-hydroxybenzofuran-5-ylisopropylaminosulfonate.

6. The compound of claim 1 which is 2,3-dihydro-3,3-dimethyl-2-hydroxybenzofuran-5-yldimethylaminosulfonate.

7. The compound of claim 1 which is 2,3-dihydro-3,3-dimethyl-2-hydroxybenzofuran-5-yldiethylaminosulfonate.

8. The compound of claim 1 which is 2,3-dihydro-3,3-dimethyl-2hydroxybenzofuran-5-ylaminosulfonate.

9. The compound of claim 1 which is 2,3-dihydro-3-ethyl-2-hydroxybenzofuran-5-ylmethylaminosulfonate.

10. The compound of claim 1 which is 2,3-dihydro-3,3-dimethyl-2-methoxybenzofuran-5-ylmethylaminosulfonate.

11. The compound of claim 1 which is 2,3-dihydro-3,3-dimethyl-2-ethoxybenzofuran-5-ylmethylaminosulfonate.

12. The compound of claim 1 which is 2,3-dihydro-3,3-dimethyl-2-propoxybenzofuran-5-ylmethylaminosulfonate.

13. The compound of claim 1 which is 2,3-dihydro-3,3-dimethyl-2-isopropoxybenzofuran-5-ylmethylaminosulfonate.

14. The compound of claim 1 which is 2,3-dihydro-3,3-dimethyl-2-methoxybenzofuran-5-ylethylaminosulfonate.

15. The compound of claim 1 which is 2,3-dihydro-3,3-dimethyl-2-ethoxybenzofuran-5-ylethylaminosulfonate.

16. The compound of claim 1 which is 2,3-dihydro-3,3-dimethyl-2-propoxybenzofuran-5-ylethylaminosulfonate.

17. The compound of claim 1 which is 2,3-dihydro-3,3-dimethyl-2-isopropoxybenzofuran-5-ylethylaminosulfonate.

18. The compound of claim 1 which is 2,3-dihydro-3,3-dimethyl-2-methoxybenzofuran-5-ylpropylaminosulfonate.

19. The compound of claim 1 which is 2,3-dihydro-3,3-dimethyl-2-ethoxybenzofuran-5-ylpropylaminosulfonate.

20. The compound of claim 1 which is 2,3-dihydro-3,3-dimethyl-2-propoxybenzofuran-5-ylpropylaminosulfonate.

21. The compound of claim 1 which is 2,3-dihydro-3,3-dimethyl-2-isopropoxybenzofuran-5-ylpropylaminosulfonate.

22. The compound of claim 1 which is 2,3-dihydro-3,3dimethyl-2-methoxybenzofuran-5-ylisopropylaminosulfonate.

23. The compound of claim 1 which is 2,3-dihydro-3,3-dimethyl-2-ethoxybenzofuran-5-ylisopropylaminosulfonate.

24. The compound of claim 1 which is 2,3-dihydro-3,3-dimethyl-2-propoxybenzofuran-5-ylisopropylaminosulfonate.

25. The compound of claim 1 which is 2,3-dihydro-3,3-dimethyl-2-isopropoxybenzofuran-5-ylisopropylaminosulfonate.

26. The compound of claim 1 which is 2,3-dihydro-3,3-dimethyl-2-methoxybenzofuran-5-ylaminosulfonate.

27. The compound of claim 1 which is 2,3-dihydro-3,3-dimethyl-2-ethoxybenzofuran-5-ylaminosulfonate.

28. The compound of claim 1 which is 2,3-dihydro-3,3-dimethyl-2-propoxybenzofuran-5-ylaminosulfonate.

29. The compound of claim 1 which is 2,3-dihydro-3,3-dimethyl-2-isopropoxybenzofuran-5-ylaminosulfonate.

30. The compound of claim 1 which is 2,3-dihydro-3,3-dimethyl-2-methoxybenzofuran-5-yldimethylaminosulfonate.

31. The compound of claim 1 which is 2,3-dihydro-3,3-dimethyl-2-ethoxybenzofuran-5-yldimethylaminosulfonate.

32. The compound of claim 1 which is 2,3-dihydro-3,3-dimethyl-2-propoxybenzofuran-5-yldimethylaminosulfonate.

33. The compound of claim 1 which is 2,3-dihydro-3,3-dimethyl-2-isopropoxybenzofuran-5-yldimethylaminosulfonate.

34. The compound of claim 1 which is 2,3-dihydro-3,3-dimethyl-2-methoxybenzofuran-5-yldiethylaminosulfonate.

35. The compound of claim 1 which is 2,3-dihydro-3,3-dimethyl-2-ethoxybenzofuran-5-yldiethylaminosulfonate.

36. The compound of claim 1 which is 2,3-dihydro-3,3-dimethyl-2-propoxybenzofuran-5-yldiethylaminosulfonate.

37. The compound of claim 1 which is 2,3-dihydro-3,3-dimethyl-2-isopropoxybenzofuran-5-yldiethylaminosulfonate.

38. The compound of claim 1 which is 2,3-dihydro-3,3-dimethyl-2-methoxybenzofuran-5-ylmethylethylaminosulfonate.

39. The compound of claim 1 which is 2,3-dihydro-3,3-dimethyl-2- -chloroethoxybenzofuran5-yldimethylaminosulfonate.

40. The compound of claim 1 which is 2,3-dihydro-3,3-dimethyl-2- -methoxyethoxybenzofuran-5-yldimethylaminosulfonate.

41. The compound of claim 1 which is 2,3-dihydro-3,3-dimethyl-2-allyloxybenzofuran-5-yldimethylaminosulfonate.

42. The compound of claim 1 which is 2,3-dihydro-3,3-dimethyl-2- -chloreothoxybenzofuran-5-ylmethylaminosulfonate.

43. The compound of claim 1 which is 2,3-dihydro-3,3-dimethyl-2-allyloxybenzofuran-5-ylmethylaminosulfonate.

44. The compound of claim 1 which is 2,3-dihydro-3,3-dimethyl-2-propargyloxybenzofuran-5-ylmethylaminosulfonate.

45. The compound of claim 1 which is 2,3-dihydro-3,3-dimethyl-2-allyloxybenzofuran-5-yldiethylaminosulfonate.

46. The compound of claim 1 which is 2,3-dihydro-3,3-dimethyl-2-chloroacetyloxybenzofuran-5-yldiethylaminosulfonate.

47. The compound of claim 1 which is 2,3-dihydro-3,3-dimethyl-2-methylcarbamoyloxybenzofuran-5-yldiethylaminosulfonate.

48. The compound of claim 1 which is 2,3-dihydro-3,3-dimethyl-2-ethylcarbamoyloxybenzofuran-5-yldiethylaminosulfonate.

49. The compound of claim 1 which is 2,3-dihydro-3,3-dimethyl-2-isopropylcarbamoyloxybenzofuran-5-yldimethylaminosulfonate.

50. The compound of claim 1 which is 2,3-dihydro-3,3-dimethyl-2-methylcarbamoyloxybenzofuran-5-yldimethylaminosulfonate.

51. The compound of claim 1 which is 2,3-dihydro-3,3-dimethyl-2-chloroacetyloxybenzofuran-5-yldimethylaminosulfonate.

52. The compound of claim 1 which is 2,3-dihydro-3,3-dimethyl-2-acetyloxybenzofuran-5-yldimethylaminosulfonate.

* * * * *